US00PP16986P2

(12) United States Plant Patent
Korlipara

(10) Patent No.: US PP16,986 P2
(45) Date of Patent: Aug. 15, 2006

(54) ***VERBASCUM* PLANT NAMED 'DARK EYES'**

(50) Latin Name: ***Verbascum* hybrid**
Varietal Denomination: Dark Eyes

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 110 days.

(21) Appl. No.: 11/081,286

(22) Filed: Mar. 15, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman LLP

(57) ABSTRACT

A new and distinct *Verbascum* plant characterized by numerous light yellow colored flowers with purple eyes on very short, upright flowering stems, a compact habit, and excellent vigor.

1 Drawing Sheet

Botanical denomination: *Verbascum* hybrid ((*V. phoeniceum*×*dumulosum*)×*V. chaixii* 'Album').

Variety designation: 'Dark Eyes'.

The present invention relates to a new and distinct cultivar of *Verbascum* hybrid, and given the cultivar name 'Dark Eyes'. *Verbascum* is in the family Scrophulariaceae.

This new cultivar originated from a cross between *Verbascum* 'Jackie' (an unpatented plant) as the seed parent and *Verbascum chaixii* 'Album' (an unpatented plant) as the pollen parent. *Verbascum* 'Jackie' is a cross between *Verbascum phoeniceum* and *Verbascum dumulosum.*

This new *Verbascum* hybrid is unique in its light yellow flowers with purple eyes combined with its extremely compact habit and very short, multiple flowering stems.

This plant is characterized by the following:

1. Light yellow flowers with purple eyes.
2. Compact habit.
3. Deep green, rugose leaves.
4. Short flowering stems.
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of a two year old *Verbascum* 'Dark Eyes' grown in the trial field in bloom in late spring.

DETAILED PLANT DESCRIPTION

The following is a detailed description of the new *Verbascum* selection based on observations of two-year-old specimens grown in the ground in full sun under typical outdoor conditions in the trial fields in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart.

Plant:

*Type.*—Herbaceous perennial.
*Form.*—Clumping basal rosette.
*Hardiness.*—U.S.D.A. Hardiness Zones 5–9.
*Size.*—16 cm tall and 30 cm wide, not including inflorescence.
*Vigor.*—Excellent.
*Roots.*—Multiple thick, fleshy roots from the crown, with freely branching laterals, white in color. Plants may be multiplied from crown divisions.

Leaf:

*Type.*—Simple.
*Arrangement.*—Basal.
*Shape.*—Ovate.
*Blade size.*—Grows to 17 cm long and 9 cm wide.
*Venation.*—Pinnate.
*Margins.*—Crenate, somewhat undulate.
*Apex.*—Acute.
*Base.*—Oblique.
*Texture.*—Leathery, thick.
*Surface texture.*—Stellate pubescent, rugose.
*Petiole.*—Length — Grows to 1 cm. Width — Grows to 8 mm. Surface — Stellate pubescent. Color — Yellow Green 145D.
*Leaf color.*—Abaxial — Deep green, Between Green 139A and Yellow Green 147A with lighter main vein, Yellow Green 145D. Adaxial — Yellow Green 147B.

Inflorescence:

*Type.*—Panicle.
*Total panicle size.*—15 cm wide and 28 cm high (where flowers are).
*Number of panicles per plant.*—8, much branched.
*Cauline leaves.*—6 cm long and 4 cm wide and smaller.
*Flower number.*—Count of 70 flowers on one panicle terminal branch.

*Peduncle*.—Height — 35 cm. Diameter — 8 mm near base. Surface — Stellate and glandular pubescent. Color — Yellow Green 146B.

*Pedicel*.—Length — 8 to 12 mm. Surface — Stellate and glandular pubescent. Color — Yellow Green 146A to B.

*Bloom time*.—May to August in Canby, Oreg.

Flower bud:

*Size*.—10 mm wide and 10 mm deep.

*Description*.—Pentagonal cushion.

*Surface*.—Glandular pubescent.

*Color*.—Yellow, Yellow 12B.

Flower:

*Type*.—Perfect. Complete. Irregular.

*Shape*.—Rotate, irregular, short tubular.

*Size*.—28 mm wide and 12 mm deep including stamens.

*Color*.—Light yellow with a purple eye, Yellow 10A with Red Purple 71A.

*Corolla*.—Petal description — 5 lobes, broadly ovate, margins entire, apices obtuse. Size — 28 mm wide and 3 mm deep. Surface — Backs are glandular pubescent, inside glabrous.

*Calyx*.—Sepal number — 5 lobes. Size — 10 mm wide and 3 mm deep. Surface — Stellate and glandular pubescent on both sides. Color — Yellow Green 146A.

*Stamens*.—Number — 5. Filaments — 7 mm long and heavily bearded Purple 77A. Anthers — Kidney shaped. Orange 26A. Pollen — Orange 28A.

*Style*.—11 mm long, Greyed Red 182B.

*Stigma*.—Yellow Green 146D.

*Fragrance*.—None.

Fertility: Sterile, no fruit or seed produced.

Disease and pests: *Verbascum* are susceptible to fungal leaf spots and root rots. They susceptible to root rots if good drainage is not available. Caterpillars may be a problem.

COMPARISONS

Compared to the pollen parent, *Verbascum chaixii*, this new cultivar has much shorter flowering stems and much larger flowers, which are light yellow rather than white. Compared the seed parent, *Verbascum* 'Jackie', the new variety is much shorter, and the flowers are light yellow rather than peach colored flowers.

There are no similar hybrids or species on the market.

I claim:

1. A new and distinct *Verbascum* plant as herein illustrated and described.

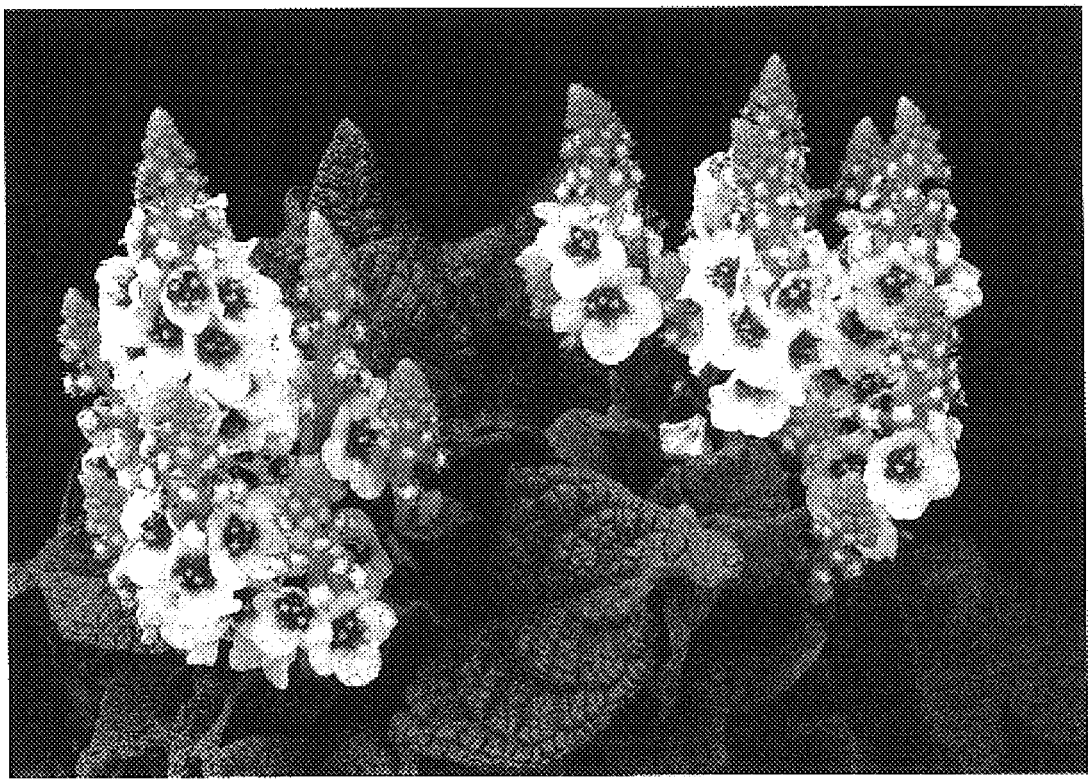

* * * * *